May 22, 1973 YOSHIO NISHIMOTO ET AL Plant Pat. 3,343
CHRYSANTHEMUM PLANT
Filed Sept. 14, 1971
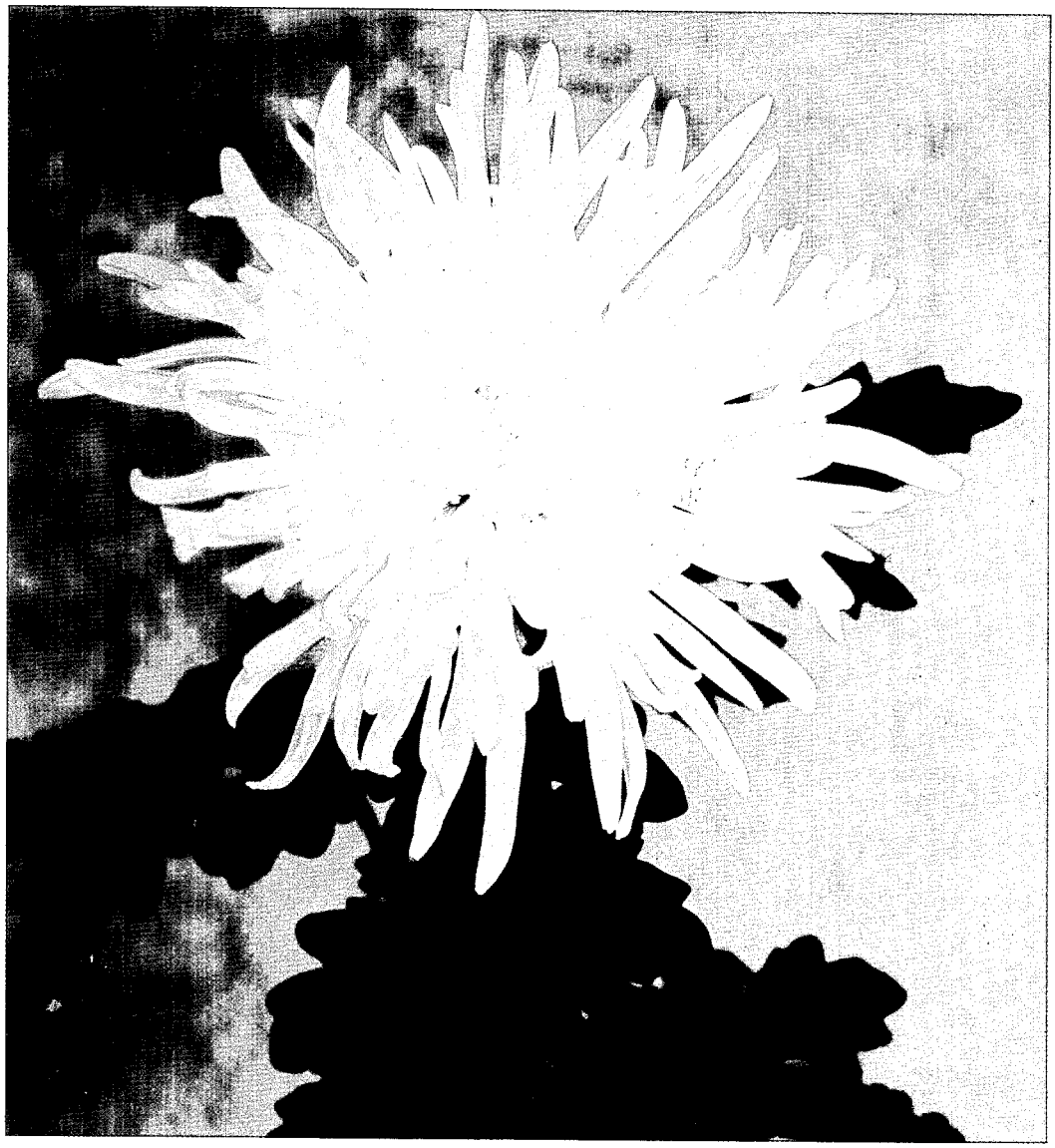

United States Patent Office

Plant Pat. 3,343
Patented May 22, 1973

3,343
CHRYSANTHEMUM PLANT

Yoshio Nishimoto, Mountain View, Calif., and Walter H. Jessel, Jr., Doylestown, and William E. Duffett, Akron, Ohio, assignors to Yoshio Nishimoto, Mountain View, Calif.

Filed Sept. 14, 1971, Ser. No. 180,531
Int. Cl. A01h *5/00*
U.S. Cl. Plt.—78 1 Claim

The present invention comprises a new and distinct cultivar of chrysanthemum plant which is a sport of the unpatented but commercially well known cultivar Fuji Mefo.

The new cultivar is similar in many respects to the parent cultivar Fuji Mefo, having the same characteristics of:

(1) Vigor and response.
(2) Fuji or spider flower form.
(3) Foliage shape and color.
(4) Same recommended period of flowering.
(5) A similar petal count.

and when asexually reproduced by cuttings at Barberton, Ohio, has been found to retain its distinctive characteristics through successive propagations.

The new cultivar when grown in the vicinity of Barberton, Ohio, has a response period of approximately 10 weeks, and the following detailed description is based on observations made of the new cultivar in a greenhouse in Barberton, Ohio. The response time, blooming period, color, and total vigor may vary significantly with varying environmental conditions such as temperature, day length, and light intensity. Suggested flowering in the northern western United States and coastal California is from October through May.

The accompanying drawing shows the unique characteristics of the new cultivar, the color being as nearly true as possible with color illustrations of this type.

In the description which follows, color references are to the Munsell Color Book, 1963 edition, and comparisons are made with the parent cultivar Fuji Mefo. Where only a single value or description appears for the new cultivar, the same applies to the parent cultivar.

BOTANICAL CLASSIFICATION: *CHRYSANTHEMUM MORIFOLIUM*

| | Yellow Fuji Mefo | Fuji Mefo |
|---|---|---|
| Bloom: | | |
| Size | Approximately 7½″ | Approximately 7″. |
| Fully expanded | Approximately 8″ | Approximately 7½″. |
| Borne | Singly on disbudded plants | |
| Stems | Strongly and sturdy | |
| Form | Spider | |
| Permanence | 10–14 days | |
| Color: | | |
| Center of flower | Yellow, 7.5Y8.5/8 | Light yellow, 7.5Y9/6. |
| Base of petals | Green yellow, 2.5GY8/10 | Green yellow, 2.5GY8/10. |
| Inside of petals | Light yellow, 7.5Y9/4 | Ivory, 10Y9/1. |
| Reverse of petals | Light yellow, 7.5Y9/6 to 7.5Y9/4. | Light yellow, 7.5Y9/4 to ivory, 10Y9/1. |
| Tonality from a distance | Light yellow | Ivory. |
| Discoloration | Light yellow, 7.5Y9/4 | Ivory, 10Y9/1. |
| Petals: | | |
| Texture | Smooth | |
| Appearance & form | Straight tubular, incurving slightly to sharp point, with petal tube being smaller in diameter than petal tube of Fuji Mefo. | |
| Arrangement | Composite, whorled on a single receptacle | |
| Persistence | Resists shatter | |
| Fragrance | Typical chrysanthemum | |
| Reproductive organs: | | |
| Stamen, anthers | None | |
| Pollen | do | |
| Arrangement | Clustered in center of flower, if present | |
| Styles | Present ray florets | |
| Length | Short | |
| Ovaries | At the base of petal attached to receptacle | |
| Plant: | | |
| Form | Herbaceous | |
| Growth | Upright | |
| Height | Approximately 36″ when grown as a single stem crop given 3–6 long day weeks and 13–16 weeks total crop time during the various seasons of the year as defined in the timetables published by Yoder Bros., Inc. | |
| Spread | None | |
| Foliage: | | |
| Top side | Very dark green, 7.5GY3/4 | |
| Size | 8½″ long, 4″ wide | 6½″ to 7½″ long, 4″ wide. |
| Quantity | Numerous | |
| Shape | Spatulate lobed | |
| Texture | Smooth | |
| Ribs & veins | Prominent | |
| Edge | Deeply indented | |
| Serration | Coarse | |
| Under side | Light green, 7.5GY5/4 | |
| Stipules | Prominent | |

The new cultivar is distinguished from Fuji Mefo by the following characteristics, when grown under comparable conditions:

(1) Its light yellow color.
(2) Flowers approximately ½″ larger.
(3) A petal tube narrower in diameter, providing a more delicate appearance.
(4) The petal tip has considerable twisting to the side rather than upward turning as in the parent variety.

The new cultivar was discovered at Mt. View, Calif.,

We claim:

1. A new and distinct cultivar of chrysanthemum characterized particularly as to its uniqueness when compared to the parent cultivar Fuji Mefo by its light yellow flower color, approximately ½″ larger flowers, and by its petal tubes which are narrower in diameter thereby providing a more delicate appearance.

No references cited.

ROBERT E. BAGWILL, Primary Examiner